United States Patent [19]

Nakanishi

[11] 4,371,341
[45] Feb. 1, 1983

[54] DENTAL HANDPIECE

[75] Inventor: Takasuke Nakanishi, Kanuma, Japan

[73] Assignee: Nakanishi Dental Mfg. Co. Ltd., Kanuma, Japan

[21] Appl. No.: 253,359

[22] Filed: Apr. 13, 1981

[51] Int. Cl.³ .............................................. A61C 1/07
[52] U.S. Cl. .................................................... 433/118
[58] Field of Search ................ 433/118, 122, 127, 124

[56] References Cited

U.S. PATENT DOCUMENTS 2,135,933 11/1938 Blair .................................... 433/122
3,552,022 1/1971 Axelsson ............................ 433/122

FOREIGN PATENT DOCUMENTS 46-602316 4/1971 Japan .

*Primary Examiner*—Robert Peshock
*Attorney, Agent, or Firm*—Armstrong, Nikaido, Marmelstein & Kubovcik

[57] ABSTRACT

The present dental handpiece generally comprises a handle portion, a powerhead assembly integrally and perpendicularly linked to the handle portion, a bushing integrally inserted into the handle portion, a rotating driving shaft journaled for rotation by means of a sleeve in the bushing, the rotating driving shaft having an integral circular disc at its top end portion, the circular disc carrying around its periphery a pinion lug which is parallel to both the disc and the rotating driving shaft, a hollow cylinder kept in motion inside the powerhead assembly at its top end held by a bushing and at its lower end by a bushing cap respectively, the rotating driving shaft having an arc-shaped longitudinal slot, a roller bearing slidably inserted into the slot and the pinion lug being slidably inserted into the central horizontal opening of the roller bearing to couple the rotating driving shaft to the rotating driven shaft whereby a drilling tool is driven to rotate in one direction and in the opposite direction alternately through a circular rotation of the driving shaft.

3 Claims, 5 Drawing Figures

U.S. Patent  Feb. 1, 1983  4,371,341
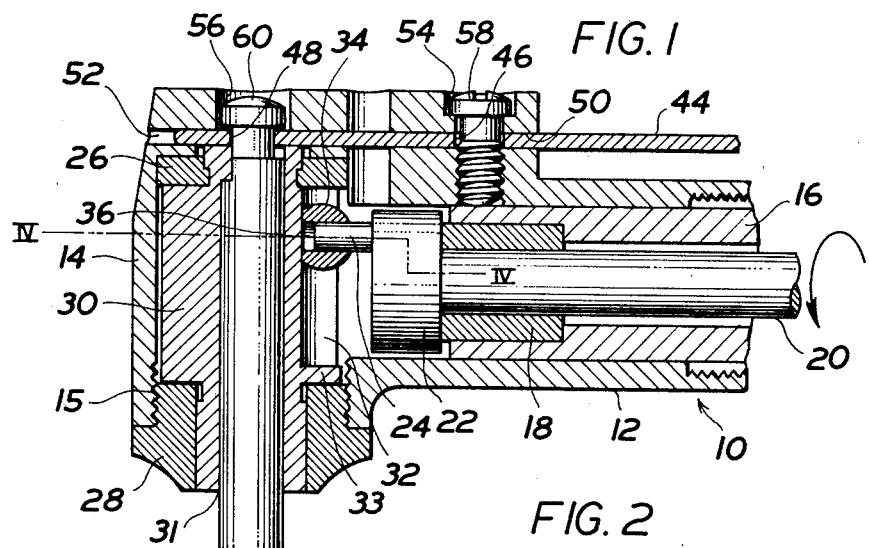
FIG. 1
FIG. 2
FIG. 3
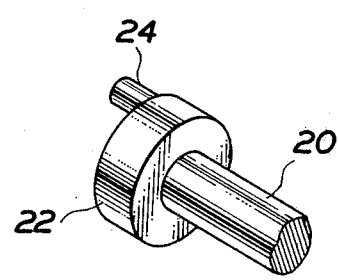
FIG. 4
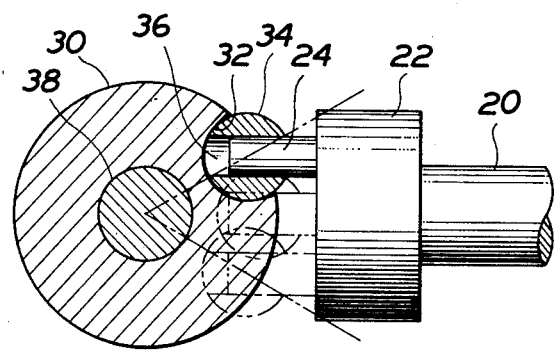
FIG. 5
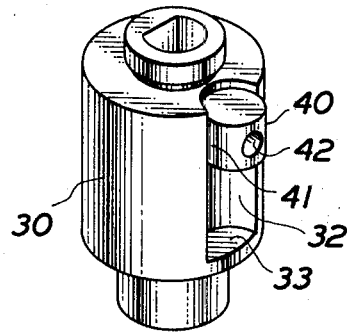

DENTAL HANDPIECE

BACKGROUND OF THE INVENTION

This invention relates to improvements in a dental handpiece for the treatment of root canals, and more particularly in a dental handpiece for the enlarging of root canals.

For the treatment and in particular for enlarging of root canals, a dental tool must be driven to rotate alternately in one direction and in the other direction coupled with an up and down movement.

According to the conventional dental handpiece, a driving shaft rotatably held in a sleeve is fixed with a circular disc which carries around its periphery a pinion lug, and perpendicularly to the axis of the driving shaft, and in the interior of a case of a drilling tool is mounted a hollow circular cylinder having a longitudinal guide slot. The hollow cylinder is made integral with the tool, while the pinion lug is mounted in such a way as to slide alternatively or reciprocally in the guide slot when the disc rotates continuously. Through the continuous rotation of the disc, reciprocating rotary movement is achieved around a perpendicular axis of the cylinder bearing so that the drilling tool may rotates about every one quarter turn.

It has been found, however, that the pinion lug coupled into the longitudinal slot of the cylinder reciprocates in direct contact with the inner wall of the slot so that the unsmooth alternate rotational movement is effected to cause severe wearing out both for the longitudinal guide slot and the pinion lug. In addition, the pinion lug may unhook easily out of the longitudinal guide slot at the two extreme positions of the slot.

A principal object of this invention is to provide a dental handpiece for the treatment of root canals whereby dental tools such as drills, buffers, reamers, or the like can be effectively driven to rotate alternately in one direction and in the other direction coupled with an up and down movement.

Another object of this invention is to provide a dental handpiece for the treatment of root canals whereby a rotating driving shaft is indirectly coupled with a hollow cylinder holding a dental tool by means of a roller bearing such as a ball bearing rotatably held in the longitudinal slot of the hollow cylinder so as to achieve smooth alternating rotational movement.

A further object of this invention is to provide a dental handpiece whereby abrasion of the roller bearing and of the pinion lug as well as a possible unhooking of the pinion lug can be prevented at the two extreme positions of the slot.

A further object of this invention is to provide a dental handpiece which will enable the dentist to carry out a treatment with tactile sense of his fingers.

A still another object of this invention is to provide a device suitable for the aforementioned purposes which will be comparatively simple in construction and at the same time desirably rigid, strong and durable.

BRIEF DESCRIPTION OF DRAWINGS

While I have shown in the accompanying drawings, a preferred embodiment of my invention, it should be understood that the same is susceptible of modification and change without departing from the spirit of my invention.

FIG. 1 is a fragmentary enlarged vertical sectional view of an embodiment of the dental handpiece, as contemplated in a preferred embodiment of the present invention;

FIG. 2 is a fragmentary enlarged perspective view of a hollow cylinder and a ball bearing rotatably coupled thereto, both being rotatably inserted into a powerhead assembly;

FIG. 3 is an enlarged partial perspective view of a top portion of a rotating driving shaft;

FIG. 4 is a cross section, on an enlarged scale, taken along a line IV—IV of FIG. 1; and FIG. 5 is an enlarged perspective view of another embodiment of a hollow cylinder and a disc roller coupled thereto for connection to a rotating driving shaft.

DETAILED DESCRIPTION

Referring to FIGS. 1, 2 and 3, a preferred embodiment which has been selected to illustrate this invention comprises a dental handpiece 10 including a handle portion 12 and a powerhead assembly 14 which is integrally and perpendicularly linked to the handle portion.

Integrally inserted into the handle portion 12 of the dental handpiece 10 is a bushing 16, through which a rotating driving shaft 20 having an integral circular disc 22 at its top end portion is journaled for rotation by means of a sleeve 18 in the bushing. The circular disc 22 carries around its periphery a pinion lug 24 which is parallel to both the disc and the rotating driving shaft 20.

Perpendicularly to the axis of the rotating driving shaft 20, and in the interior of the powerhead assembly 14 is mounted a hollow cylinder 30 having a longitudinal arc-shaped slot 32. The hollow cylinder 30 is kept in motion inside the powerhead assembly 14 at its top end driven by a bushing 26 and at its lower end by a bushing cap 28 respectively. As shown in FIG. 1, the bushing cap 28 is threadedly mounted into a screw thread 15 around an inner end periphery of the powerhead assembly 14.

As particularly shown in FIGS. 1 and 2, a lower end portion of the longitudinal arc-shaped slot 32 has a bottom 33. A roller such as a ball bearing 34 having a spherical surface to coincide with the arc-shaped slot 32 and also having a central horizontal opening 36 is slidably inserted into the slot 32 from its upper inlet.

The pinion lug 24 of the circular disc 22 is slidably inserted into the central horizontal opening 36 of the ball bearing 34 to couple the driving shaft 20 with the hollow cylinder 30. In this way, the ball bearing 34 together with the pin 24 is so mounted as to slide alternately or reciprocally in the slot 32 when the cylindrical disc 22 rotates continuously, thus enabling to allow alternately vertical and reciprocal rotation within a given angle of a drilling tool 38 firmly held into the hollow cylinder 30.

The bottom 33 at the lower end portion of the slot 32 prevents the ball bearing 34 from dropping down out of the slot.

Referring to FIG. 5 showing another embodiment of this invention, a disc roller 40 having a right cylindrical surface 41 to coincide with the arc-shaped longitudinal slot 32 and also having a mid horizontal opening 42 is slidably inserted into the slot 32. As in the embodiments shown in FIGS. 1–4, the cylindrical pin 24 of the circular disc 22 is slidably inserted into the central horizontal opening 42 to couple the rotating driving shaft 20 with the hollow cylinder 30.

Slits 50 and 52 are cut at a top portion of the handle portion 12 and parallelly to the rotating driving shaft 20, and a pair of bores 54 and 56 are vertically formed to cross the slits 50 and 52 respectively, the bore 56 being provided to abut upon a longitudinal hollow 31 of the hollow cylinder 30. A spiral is formed around an inner periphery of the grooved bore 54.

A locking plate 44 having a pair of openings 46 and 48 to coincide with the bores 54 and 56 respectively is slidably inserted into the slits 50 and 52. A screw 58 is set into the opening 48 and the bore 54 to fix the locking plate 44.

Held into the longitudinal hollow 31 is the drilling tool 38, which is fastened by a screw 60 set into a top portion of the tool through the ungrooved bore 56 and the opening 46 so that the tool is kept at right angle to the axis of the driving shaft 20. Thus, the drilling tool 38 is prevented from slipping along the axis of the cylinder 30 and disengaging therefrom.

Through a continuous circular rotation around the axis of the driving shaft 20 into one direction, the arrangement of this invention provides alternate rotary motion around a perpendicular axis of the hollow cylinder 30 so that the drilling tool 38 is driven to rotate in one direction and in the opposite direction alternately. Through the intermediary of the ball bearing 34 or the disc roller 40, unhooking of the pin 24 at the two extreme positions of the slot 32 can be prevented and the smooth alternate rotation of the drilling tool 38 may be ensured.

I claim:

1. A dental handpiece for the treatment of root canals comprising: a handle portion; a powerhead assembly integrally and perpendicularly linked to said handle portion; a bushing integrally inserted into said handle portion; a rotating driving shaft journaled for rotation by means of a sleeve in said bushing, said rotating driving shaft having an integral circular disc at its top end portion, said circular disc carrying around its periphery a pinion lug which is parallel to both said disc and said rotating driving shaft; a hollow cylinder kept in motion inside said powerhead assembly at its top end held by a bushing and at its lower end by a bushing cap respectively, said hollow cylinder being perpendicular to the axis of said rotating driving shaft and also having an arc-shaped longitudinal slot; a ball bearing slidably inserted into said slot having a spherical surface to coincide with the arc-shaped slot and slidably inserted into said longitudinal slot, said ball bearing having a central horizontal opening; said pinion lug of said circular disc being slidably inserted into the central horizontal opening of said ball bearing so as to couple said rotating driving shaft with said hollow cylinder; said handle portion being provided with a pair of slits at its top portion and parallelly to said rotating driving shaft; said top portion being also formed with a pair of bores vertically to cross said slits respectively, one of said bores being provided to abut upon a longitudinal hollow of said hollow cylinder; another bore being provided with a spiral groove; a locking plate having a pair of openings to coincide with said bores and slidably inserted into said slits; a screw threadedly set into said grooved bore and said neighboring slit to fix said locking plate; and a drilling tool firmly held into said longitudinal hollow of said cylinder and fastened by a screw set into a top portion of said drilling tool through said ungrooved bore and said neighboring opening so as to keep said drilling tool at right angle to the axis of said rotating driving shaft whereby said drilling tool is driven to rotate in one direction and in the opposite direction alternately through a continuous circular rotation of said driving shaft.

2. A dental handpiece for the treatment of root canals comprising: a handle portion; a powerhead assembly integrally and perpendicularly linked to said handle portion; a rotating driving shaft journaled for rotation by means of a sleeve in said bushing, said rotating driving shaft having an integral circular disc at its top end portion, said circular disc carrying around its periphery a pinion lug which is parallel to both said disc and said rotating driving shaft; a hollow cylinder kept in motion inside said powerhead assembly at its top end held by a bushing and at its lower end by a bushing cap respectively, said hollow cylinder being perpendicular to the axis of said rotating driving shaft and also having an arc-shaped longitudinal slot; a disc roller slidably inserted into said slot having a cylindrical surface to coincide with the arc-shaped slot and slidably inserted into said longitudinal slot, said disc roller having a central horizontal opening; said pinion lug of said circular disc being slidably inserted into the central horizontal opening of said cylindrical disc roller so as to couple said rotating driving shaft with said hollow cylinder; said handle portion being provided with a pair of slits at its top portion and parallelly to said rotating driving shaft; said top portion being also formed with a pair of bores vertically to cross said slits respectively, one of said bores being provided to abut upon a longitudinal hollow of said hollow cylinder; another bore being provided with a spiral groove; a locking plate having a pair of openings to coincide with said bores and slidably inserted into said slits; a screw threadedly set into said grooved bore and said neighboring slit to fix said locking plate; and a drilling tool firmly held into said longitudinal hollow of said cylinder and fastened by a screw set into a top portion of said drilling tool through said ungrooved bore and said neighboring opening so as to keep said drilling tool at right angle to the axis of said rotating driving shaft whereby said drilling tool is driven to rotate in one direction and in the opposite direction alternately through a continuous circular rotation of said driving shaft.

3. A dental handpiece for the treatment of root canals as set forth in claim 1 or 2 wherein a lower portion of said longitudinal arc-shaped slot is bottomed to prevent said ball bearing or disc roller from dropping down out of said slot.

* * * * *